United States Patent
Schreivogel

(10) Patent No.: US 9,846,138 B2
(45) Date of Patent: Dec. 19, 2017

(54) BROADBAND LAMBDA PROBE AND PRODUCTION METHOD FOR A BROADBAND LAMBDA PROBE

(71) Applicant: Robert Bosch GmbH, Stuttgart (DE)

(72) Inventor: Martin Schreivogel, Bad Berka (DE)

(73) Assignee: Robert Bosch GmbH, Stuttgart (DE)

(*) Notice: Subject to any disclaimer, the term of this patent is extended or adjusted under 35 U.S.C. 154(b) by 346 days.

(21) Appl. No.: 14/590,481

(22) Filed: Jan. 6, 2015

(65) Prior Publication Data
US 2015/0198558 A1    Jul. 16, 2015

(30) Foreign Application Priority Data
Jan. 14, 2014    (DE) .................. 10 2014 200 481

(51) Int. Cl.
     *G01N 27/409*      (2006.01)
     *G01N 27/41*      (2006.01)
     *G01N 27/419*      (2006.01)

(52) U.S. Cl.
     CPC ........... *G01N 27/409* (2013.01); *G01N 27/41* (2013.01); *G01N 27/419* (2013.01); *Y10T 29/49002* (2015.01)

(58) Field of Classification Search
     CPC ........ G01N 27/22–27/24; G01N 27/41; G01N 27/417; G01N 27/419; G01N 27/409; G01N 2027/22; Y10T 29/49002
     See application file for complete search history.

(56) References Cited

U.S. PATENT DOCUMENTS

| | | | | |
|---|---|---|---|---|
| 4,915,084 A | * | 4/1990 | Gonze | .................... F02B 11/00 123/1 A |
| 5,216,409 A | * | 6/1993 | Ament | ................ B60R 16/0232 123/575 |
| 5,389,224 A | * | 2/1995 | Hetrick | ................ G01N 27/002 123/438 |
| 6,280,605 B1 | * | 8/2001 | Jach | ..................... G01N 27/417 204/425 |

FOREIGN PATENT DOCUMENTS

| | | |
|---|---|---|
| DE | 101 63 942 A1 | 7/2003 |
| DE | 10 2009 029 621 A1 | 3/2011 |
| DE | 10 2012 201 304 A1 | 8/2013 |
| DE | 10 2013 205 540 A1 | 10/2014 |

* cited by examiner

*Primary Examiner* — Gurpreet Kaur
(74) *Attorney, Agent, or Firm* — Maginot, Moore & Beck LLP

(57) ABSTRACT

A broadband lambda probe includes a measurement hollow space. The broadband lambda probe further includes an oxygen pump cell having an outer pump electrode and an inner pump electrode to enable the transfer of oxygen from the measurement hollow space to an external environment of the broadband lambda probe. The broadband lambda probe further includes a Nernst concentration cell. The broadband lambda probe further includes at least one capacitive sensor device. The at least one capacitive sensor device has a capacitance configured to be varied with a change of a concentration of at least one substance. The concentration is present in the respective at least one capacitive sensor device. The at least one capacitive sensor device is positioned in the broadband lambda probe to at least one of directly adjoin the measurement hollow space and partially project into the measurement hollow space.

12 Claims, 3 Drawing Sheets

BROADBAND LAMBDA PROBE AND PRODUCTION METHOD FOR A BROADBAND LAMBDA PROBE

This application claims priority under 35 U.S.C. §119 to patent application no. DE 10 2014 200 481.0 filed on Jan. 14, 2014 in Germany, the disclosure of which is incorporated herein by reference in its entirety.

The disclosure relates to a broadband lambda probe. The disclosure further relates to a production method for a broadband lambda probe.

BACKGROUND

DE 101 63 942 A1 describes various embodiments of broadband lambda probes. Each of the broadband lambda probes has an oxygen pump cell comprising an outer pump electrode and an inner pump electrode and a Nernst concentration cell having a Nernst electrode and a reference electrode. Each of the broadband lambda probes also has at least one HC (hydrocarbon) electrode which is arranged on the outer face of said broadband lambda probe and by means of which a hydrocarbon content of an exhaust gas in an external environment of the respective broadband lambda probe is intended to be measurable. In order to protect against aggressive constituent parts of the exhaust gas, the at least one HC electrode is provided with a porous protective layer comprising zirconium dioxide.

SUMMARY

The disclosure provides a broadband lambda probe having the features of the disclosed subject matter, and a production method for a broadband lambda probe having the features of the disclosed subject matter.

The disclosure provides broadband lambda probes which are designed for combined detection of an oxygen partial pressure (or a lambda value) and of the at least one substance. The number of sensors required to analyze a substance composition within a volume can be reduced owing to the advantageous multifunctionality of the broadband lambda probes according to the disclosure. This also reduces the amount of work involved in arranging the sensors required to analyze the substance composition within the volume. The costs for further sensors which are not required can also be saved by means of the advantageous multifunctionality of the broadband lambda probes according to the disclosure.

A significant advantage of the broadband lambda probes according to the disclosure is also that the at least one capacitive sensor device which is integrated in the respective measurement hollow space is already protected against the aggressive environmental influences (for example gases, soot, ash and/or heat) which are present in the external environment of the respective broadband lambda probe owing to the advantageous arrangement of said sensor device. Therefore, the protective layer which is conventionally required according to the prior art under these conditions is dispensed with. Therefore, the present disclosure also contributes to reducing the costs of and the production outlay on multifunctional broadband lambda probes.

A sensitivity of the at least one capacitive sensor device is also improved owing to the integration into the measurement hollow space in the broadband lambda probe according to the disclosure. In the case of the broadband lambda probe according to the disclosure, the advantage of the precisely defined and relatively low oxygen concentration within the measurement hollow space can be utilized for the measurements executed by the at least one capacitive sensor device. Since there is virtually no oxygen in the respective measurement hollow space in general, there is no risk of oxygen-related cross-influences on the measurements which are executed by the at least one capacitive sensor device. The sensitivity of the at least one capacitive sensor device is therefore considerably increased.

In one advantageous embodiment, the at least one capacitive sensor device comprises in each case a first sensor electrode, in each case a second sensor electrode and in each case at least one dielectric which is present between the first sensor electrode and the second sensor electrode. Therefore, at least one MIM structure (metal-insulator-metal structure) can be integrated into the measurement hollow space in the broadband lambda probe as the at least one capacitive sensor device. Since an MIM structure can be formed in the measurement hollow space by means of method steps which can be executed in a simple manner, the integration of the at least one capacitive sensor device into the measurement hollow space in the broadband lambda probe can be executed without any significant additional outlay. In addition, at least one MIM structure can be easily formed in the measurement hollow space in the broadband lambda probe, without a large design of the broadband lambda probe being required for this purpose.

By way of example, the at least one dielectric of the respective capacitive sensor device at least comprises silicon dioxide, aluminum dioxide, hafnium oxide, tantalum oxide, zirconium oxide, silicon nitride, boron nitride, silicon carbide, tungsten silicide and/or tantalum silicide. Therefore, the at least one dielectric can be selected from a large number of cost-effective materials which are used relatively frequently (especially in semiconductor technology).

The at least one dielectric of the respective capacitive sensor device preferably comprises at least one material which has a bias-dependent permittivity and impedance at least at a temperature equal to an operating temperature of the broadband lambda probe. In particular, the at least one dielectric of the respective capacitive sensor device comprises at least barium titanate, lead zirconate titanate and/or barium strontium titanate as the at least one material. However, other materials which are polar at least at the operating temperature, in particular other ferroelectrics, can also be used instead of or in addition to the materials listed here.

In a further advantageous embodiment, the first sensor electrode of the respective capacitive sensor device, which first sensor electrode is oriented toward the measurement hollow space, comprises at least one catalytically active material. This may improve a sensitivity of the sensor element.

By way of example, the first sensor electrode of the respective capacitive sensor device, which first sensor electrode is oriented toward the measurement hollow space, comprises gold, platinum, aluminum, palladium, rhenium, ruthenium, iridium, titanium, titanium nitride, tantalum nitride and/or rhodium as the at least one catalytically active material. However, it should be noted that the catalytically active materials listed here are to be interpreted as being merely exemplary.

In a further advantageous embodiment, the second sensor electrode of the respective capacitive sensor device, which second sensor electrode is directed away from the measurement hollow space, comprises at least one semiconductor material. The first sensor electrode of the same capacitive sensor device may, if desired, also have at least one semiconductor material, especially the same semiconductor material as the second sensor electrode.

In particular, the second sensor electrode of the respective capacitive sensor device, which second sensor electrode is directed away from the measurement hollow space, can comprise silicon, germanium, gallium arsenide, indium phosphorus, silicon carbide and/or gallium nitride as the at least one semiconductor material. The semiconductor materials listed here can also be used for the first sensor electrode. Therefore, a large number of cost-effective semiconductor materials which are frequently used in semiconductor technology can be used for producing the at least one capacitive sensor device.

The capacitance/impedance of the respective capacitive sensor device can preferably be varied by means of changing a concentration of at least one hydrogen-containing gas and/or of at least one nitrogen oxide as the at least one substance, which concentration is present at the capacitive sensor device in the measurement hollow space. The at least one capacitive sensor device can therefore be used to detect/identify, for example, hydrogen, a large number of hydrocarbons, such as propene, ammonia, nitrogen monoxide and nitrogen dioxide in particular. In particular, the broadband lambda probe according to the disclosure can therefore be advantageously used to analyze an exhaust gas in an exhaust tract of a vehicle.

The at least one capacitive sensor device is advantageously electrically connected to an evaluation device of the broadband lambda probe by means of conductor tracks. In this case, the evaluation device is preferably designed to determine a leakage current, a capacitance, a bias-dependent impedance and/or a frequency-dependent impedance at the respective capacitive sensor device. As shown below by means of an example, the at least one capacitive sensor device can therefore be reliably used for a large number of detection and measurement methods.

The advantages cited above can also be implemented by executing the corresponding production method for a broadband lambda probe. The production method can be developed in line with the above-described embodiments of the broadband lambda probe.

BRIEF DESCRIPTION OF THE DRAWINGS

Further features and advantages of the present disclosure will be explained below with reference to the figures, in which.

DETAILED DESCRIPTION

Figure 1A:
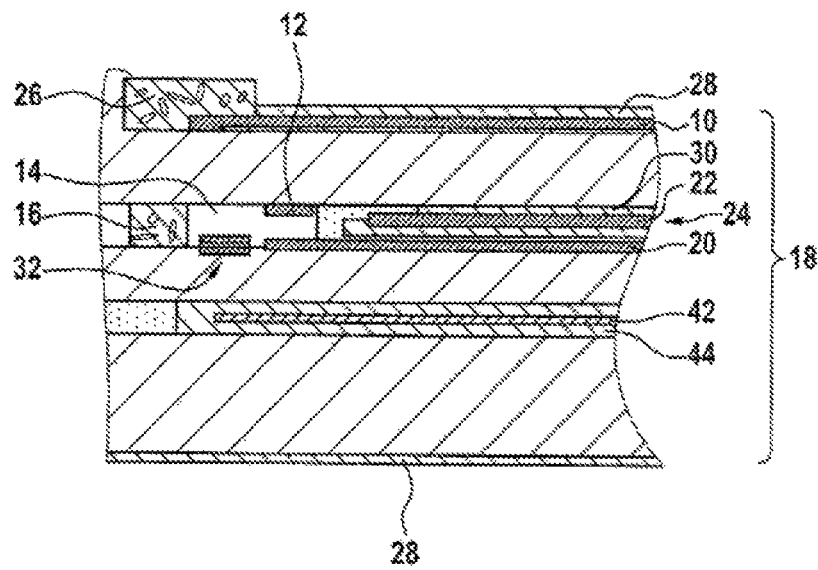
FIGS. 1a and 1b show schematic partial illustrations of an embodiment of the broadband lambda probe.
Figure 1B:
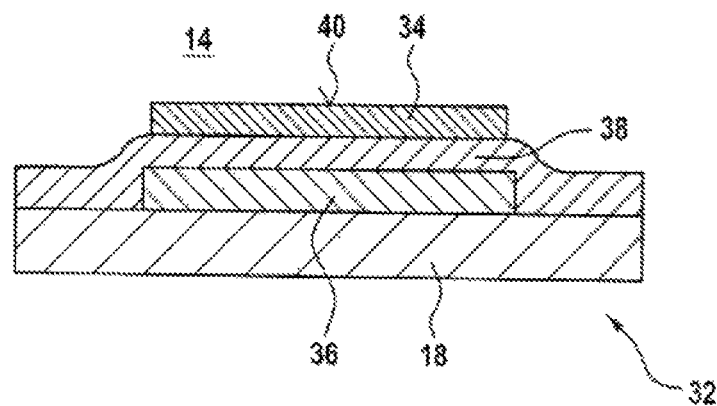

FIGS. 1a and 1b show schematic partial illustrations of an embodiment of the broadband lambda probe.

The broadband lambda probe partially illustrated in FIG. 1a has an oxygen pump cell which comprises an outer pump electrode 10 and an inner pump electrode 12. The oxygen pump cell having the pump electrodes 10 and 12 is designed to transfer oxygen from a measurement hollow space 14 in the broadband lambda probe to an external environment of the broadband lambda probe. However, since controlling the flow of oxygen across a porous diffusion barrier 16 by means of a voltage which is applied between the pump electrodes 10 and 12 is known from the prior art, the oxygen pump cell is not discussed in any detail here.

The measurement hollow space 14 is delimited from the external environment of the broadband lambda probe by the porous diffusion barrier 16. To this end, an opening which is formed in a housing/substrate structure 18 of the broadband lambda probe and which extends from the external environment to the measurement hollow space 14 can be sealed off by means of the porous diffusion barrier 16 by way of example.

The broadband lambda probe also has a Nernst concentration cell having a Nernst electrode 20 and a reference electrode 22. Since the interaction of the Nernst concentration cell with the oxygen pump cell is already known from the prior art, this is not discussed any further here. While the outer pump electrode 10 is arranged on an outer face of the broadband lambda probe, the inner pump electrode 12 and the Nernst electrode 20 are arranged directly at the measurement hollow space 14 and/or project at least partially into the measurement hollow space 14. Therefore, there is direct contact between the at least one gas which is present in the measurement hollow space 14 and the electrodes 12 and 20. The reference electrode 22 is arranged in/on a reference channel 24 which is schematically illustrated in FIG. 1a. Since the ability to form the broadband lambda probe is not limited to a specific design/arrangement of the reference channel 24, this is not discussed any further detail here.

In order to protect against aggressive environmental influences, the outer pump electrode 10 can be covered at least partially by a porous protective layer 26 and/or a non-porous protective layer 28. Other outer surfaces of the broadband lambda probe can likewise be covered by one of the protective layers 26 and 28. The reference electrode 22 can also be surrounded by at least one (porous or non-porous) protective layer 30.

The broadband lambda probe comprises at least one capacitive sensor device 32 which is arranged in the broadband lambda probe in such a way that the at least one capacitive sensor device 32 directly adjoins the measurement hollow space 14 and/or projects at least partially into the measurement hollow space 14. The at least one capacitive sensor device 32 is designed such that its capacitance can be varied by means of changing a concentration of at least one substance, which concentration is present at the respective capacitive sensor device 32 (in the measurement hollow space 14). The at least one capacitive sensor device 32 can therefore be used to identify/detect the at least one substance, in particular to measure a concentration of the at least one substance. Therefore, the broadband lambda probe can be used not only to measure the lambda value but also to identify/detect the at least one substance, in particular to determine the concentration of said substance. Other sensors which are conventionally additionally required to identify/detect the at least one substance can be saved owing to the advantageous multifunctionality of the broadband lambda probe. The need for dedicated installation spaces for gas sensors for detecting the at least one substance is also dispensed with owing to the multifunctionality of the broadband lambda probe.

Owing to the advantageous arrangement of said sensor device on/in the low-oxygen atmosphere present in the measurement hollow space 14, there is no risk of oxygen-related cross-influences on the analyses/measurements which are executed by the at least one capacitive sensor device 32. A sensitivity of the at least one capacitive sensor device 32 which is integrated in the measurement hollow space 14 is therefore particularly high.

In addition, owing to the advantageous integration of the at least one capacitive sensor device 32 into the measurement hollow space 14, less aggressive environmental influences generally occur in the immediate environment of said capacitive sensor device. Therefore, there is no need to protect the at least one capacitive sensor device 32 which is integrated into the measurement hollow space 14 against an aggressive gas in the immediate environment of said capacitive sensor device. Therefore, protective layers which are conventionally required can be saved. In addition, the advantageous integration contributes to the increase in service life/useful time of the at least one capacitive sensor device 32.

The capacitance of the respective/at least one capacitive sensor device 32 can preferably be varied by means of changing a concentration of at least one hydrogen-containing gas and/or of at least one nitrogen oxide as the at least one substance, said concentration being present at the capacitive sensor device 32 in the measurement hollow space 14. Therefore, hydrogen ($H_2$), propene ($C_3H_6$), ammonia ($NH_3$), nitrogen monoxide (NO) and nitrogen dioxide ($NO_2$), for example, can be identified/detected as the at least one substance by means of the at least one capacitive sensor device 32. In particular, the at least one capacitive sensor device 32 can be used to measure at least one concentration of the reducing or oxidizing gases listed here in this case. The broadband lambda probe can therefore be used especially to detect harmful gases which possibly occur in an exhaust tract of a motor vehicle. In particular, combustion of a fuel in an engine and/or exhaust gas after-treatment can therefore be efficiently regulated by means of the broadband lambda probe.

FIG. 1b shows an enlarged partial detail of FIG. 1a with the at least one capacitive sensor device 32. In the embodiment of FIG. 1b, the illustrated capacitive sensor device 32 has a first sensor electrode 34, a second sensor electrode 36 and at least one dielectric 38 which is present between the first sensor electrode 34 and the second sensor electrode 36. The at least one capacitive sensor device 32 can therefore be designed as an MIM structure/MIM electrode (metal-insulator-metal structure, metal-insulator-metal electrode). A capacitive sensor device 32 of this kind can be integrated into the measurement hollow space 14 in a simple manner without the size of the respective broadband lambda probe being significantly increased for this purpose.

The first sensor electrode 34 is preferably oriented toward the measurement hollow space 14. This can be understood to mean that a contact area 40 of the first sensor electrode 34, which contact area is directed away from the second sensor electrode 36, makes direct contact with the at least one gas which is present in the measurement hollow space 14. In contrast, an arrangement/orientation which is directed away from the measurement hollow space 14 is preferred for the second sensor electrode 36. Therefore, the second sensor electrode 36 is preferably fully shielded from the at least one gas present in the measurement hollow space 14 by means of the at least one dielectric 38 and the at least one sensor electrode 34. By way of example, the second sensor electrode 36 can be arranged on/fastened to a substrate of the housing/substrate structure 18.

The first sensor electrode 36 and the second sensor electrode 36 can be in the form of closed or in the form of porous metal layers. By way of example, the second sensor electrode 36 can be a closed metal layer, while the first sensor electrode 34 is of porous design. The first sensor electrode 34 which is oriented toward the measurement hollow space 14 can comprise at least one catalytically active material. In particular, the first sensor electrode 34 which is oriented toward the measurement hollow space 14 can comprise gold, platinum, aluminum, palladium, rhenium, ruthenium, iridium, titanium, titanium nitride, tantalum nitride and/or rhodium as the at least one catalytically active material. However, the materials listed here can also be used to form the second sensor electrode 36.

By way of example, the second sensor electrode 36 which is directed away from the measurement hollow space 14 comprises at least one semiconductor material. In particular, silicon, germanium, gallium arsenide, indium phosphorus, silicon carbide and/or gallium nitride can be used as the at least one semiconductor material for forming at least the second sensor electrode 36. However, if desired, the first sensor electrode 34 can also be formed from the semiconductor materials listed here or from another semiconductor material.

At least one of the sensor electrodes 34 and 36 can also be composed of a composite material (cermet) comprising at least one ceramic material in a metallic matrix. Therefore, a large number of different starting materials can be used to form wear-resistant sensor electrodes 34 and 36.

The sensor electrodes 34 and 36 are preferably formed from different materials. However, the sensor electrodes 34 and 36 can also be formed from the same material or have the same material composition. Reference is made to DE 10 2009 029 621 A1 in respect of further ways of forming/arranging the sensor electrodes 34 and 36 of the at least one capacitive sensor device 32.

The at least one dielectric 38 can comprise, for example, silicon dioxide, aluminum dioxide, hafnium oxide, tantalum oxide, zirconium oxide, silicon nitride, boron nitride, silicon carbide, tungsten silicide and/or tantalum silicide. However, the at least one dielectric 38 can also have a different electrically insulating material in addition or as an alternative to the materials listed here. The at least one dielectric 38 further preferably comprises at least one material which can be electrically polarized at a temperature equal to an operating temperature of the broadband lambda probe. In other words, the at least one material has a bias-dependent (or DC bias-dependent) permittivity and impedance at least at a temperature equal to the operating temperature of the broadband lambda probe. The at least one dielectric 38 can therefore be described as at least one thin dielectric layer which preferably contains a polarizable species. By way of example, the at least one dielectric 38 can comprise at least barium titanate, lead zirconate titanate and/or barium strontium titanate as the at least one material/the at least one polarizable species.

In addition, the broadband lambda probe can further have at least one integrated heating line 42 which is preferably embedded in an electrically insulating thermally conductive material 44. On account of its integration into the measurement hollow space 14, the at least one capacitive sensor device 32 can be heated together with other components of the broadband lambda probe by means of the at least one heating line 42 without additional outlay. Therefore, there is hardly any increase in energy consumption by the broadband lambda probe due to its being additionally equipped with the at least one capacitive sensor device 32.

The at least one capacitive sensor device 32 can be electrically connected to an evaluation device of the broadband lambda probe by means of conductor tracks (not illustrated). In particular, laminated conductor tracks can be designed to establish contact between the at least one capacitive sensor device 32 and the broadband lambda probe. Therefore, conductor tracks of a type which is also used for the at least one further electrode 10, 12, 20 and 22 of the broadband lambda probe can be used to contact-connect the at least one capacitive sensor device 32. Therefore, contact-connection of the at least one capacitive sensor device 32 is associated with hardly any additional outlay.

The evaluation device, not shown in FIGS. 1a and 1b, can be designed to tap off at least one signal from the at least one capacitive sensor device 32 and/or to receive at least one signal which is provided by the at least one capacitive sensor device 32, and to define at least one item of information relating to an ability to identify and/or relating to a concentration of the at least one substance taking into account the at least one signal. The evaluation device can then output the defined information and/or use said defined information to drive at least one apparatus, such as an injection apparatus for injecting a fuel into an internal combustion engine and/or an apparatus of an exhaust gas after-treatment system for example.

The evaluation device is preferably designed to determine a leakage current, a capacitance, a bias-dependent impedance and/or a frequency-dependent impedance at the at least one capacitive sensor device 32. (A bias-dependent and frequency-dependent impedance can also be determined by means of the evaluation device.) The advantages of a design of the evaluation device of this kind are clear from the following example.

Figure 2A:
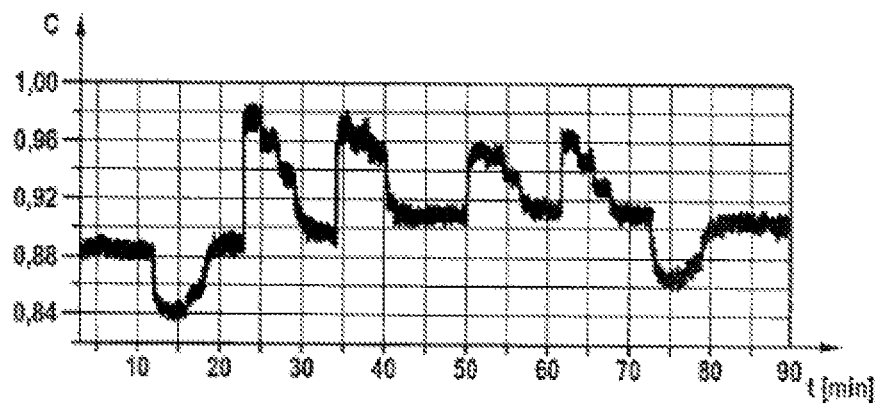
FIGS. 2a and 2b show coordinate systems illustrating a manner of operation of the above-described embodiment of the broadband lambda probe.
Figure 2B:
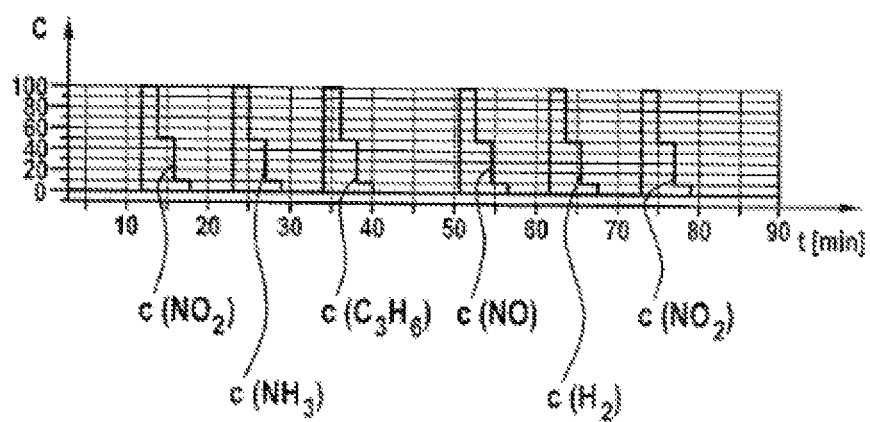

FIGS. 2a and 2b show coordinate systems for explaining a manner of operation of the above-described embodiment of the broadband lambda probe.

In the coordinate systems of FIGS. 2a and 2b, the abscissas are in each case a time axis t (in minutes). A (standardized) capacitance C is indicated by means of the ordinate of the coordinate system of FIG. 2a. An ordinate of the coordinate system of FIG. 2b describes a concentration c of various gases (in percent).

In the example in FIGS. 2a and 2b, the measurement hollow space is filled successively with nitrogen dioxide ($NO_2$) at a concentration of $c(NO_2)$, ammonia ($NH_3$) at a concentration of $c(NH_3)$, propene ($C_3H_6$) at a concentration of $c(C_3H_6)$, nitrogen monoxide (NO) at a concentration of $c(NO)$, and hydrogen ($H_2$) at a concentration of $c(H_2)$. The three stages are then repeated by nitrogen dioxide. The measurement hollow space is flushed between each filling operation with various gases.

As shown by the capacitance C illustrated in FIG. 2a, each of the listed gases, even at low concentrations, further causes a significant deviation in the capacitance C from its initial value. The broadband lambda probe is therefore suitable for identifying/detecting all of the listed gases.

Figure 3:
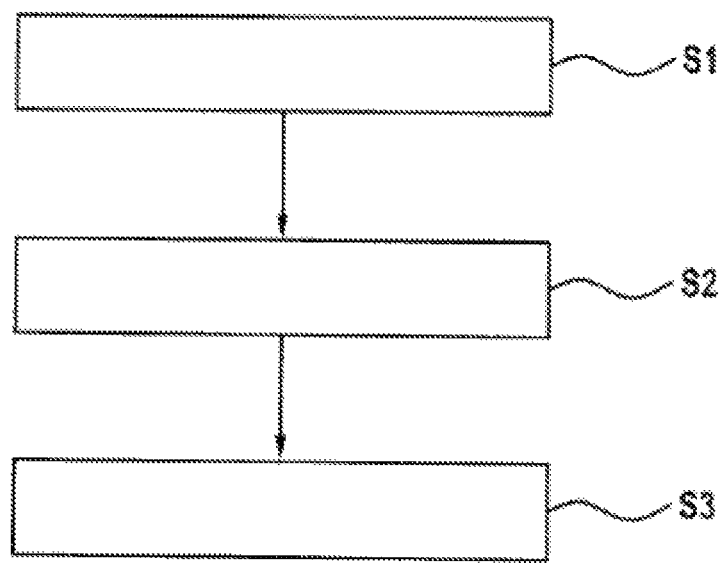
FIG. 3 shows a flowchart illustrating an embodiment of the production method for a broadband lambda probe.

FIG. 3 shows a flowchart for explaining an embodiment of the production method for a broadband lambda probe.

The production method can be executed, for example, to produce the above-described broadband lambda probe. However, the ability to execute the production method is not limited to the creation of this broadband lambda probe.

An oxygen pump cell of the broadband lambda probe with an outer pump electrode and an inner pump electrode is formed in a method step S1. This takes place in such a way that oxygen is transferred from a measurement hollow space in the broadband lambda probe to an external environment of the broadband lambda probe by means of the oxygen pump cell during operation of the broadband lambda probe. A Nernst concentration cell of the broadband lambda probe with a Nernst electrode and a reference electrode is formed in a method step S2.

In addition, at least one capacitive sensor device is formed in a method step S3, the capacitance of said sensor device being varied by means of changing a concentration of at least one substance, which concentration is present at the capacitive sensor device, during operation of the broadband lambda probe. The at least one capacitive sensor device is arranged in the broadband lambda probe in such a way that the at least one capacitive sensor device directly adjoins the measurement hollow space and/or projects at least partially into the measurement hollow space.

An advantageous way of forming the at least one capacitive sensor device as an MIM structure is already described above. The at least one dielectric of the MIM structure can be applied to at least one surface of the second sensor electrode by means of sputtering or atomic layer deposition for example. The at least one dielectric can also be deposited on the second sensor electrode by screen printing with subsequent sintering. The first sensor electrode can then be arranged on an outer face of the at least one dielectric, which outer face is directed away from the second sensor electrode.

In particular, the broadband lambda probe can also be produced using microsystem technology. The above-described production method can be executed to produce a single broadband lambda probe or to simultaneously produce a large number of broadband lambda probes. It should also be noted that the ability to execute the production method is not limited to compliance with a specific time sequence of method steps S1 to S3. The method steps S1 to S3 can be carried out in any desired order or at the same time.

What is claimed is:

1. A broadband lambda probe comprising:
   a substrate structure that defines a measurement hollow space;
   an oxygen pump cell incorporated into the substrate structure and including:
      an outer pump electrode; and
      an inner pump electrode, the outer pump electrode and the inner pump electrode configured to enable the transfer of oxygen from the measurement hollow space to an external environment of the broadband lambda probe;
   a Nernst concentration cell incorporated into the substrate structure and including:
      a Nernst electrode; and
      a reference electrode; and
   at least one capacitive sensor device incorporated into the substrate structure so as to be exposed to an atmosphere in the measurement hollow space, the at least one capacitive sensor device having a capacitance that varies with a change of a concentration of at least one substance in the measurement hollow space.

2. The broadband lambda probe according to claim 1, wherein the at least one capacitive sensor device includes a first sensor electrode, a second sensor electrode, and at least one dielectric, the at least one dielectric positioned between the first sensor electrode and the second sensor electrode.

3. The broadband lambda probe according to claim 2, wherein the at least one dielectric includes at least one of silicon dioxide, aluminum dioxide, hafnium oxide, tantalum oxide, zirconium oxide, silicon nitride, boron nitride, silicon carbide, tungsten silicide, and tantalum silicide.

4. The broadband lambda probe according to claim 2, wherein the at least one dielectric includes at least one material, the at least one material having a bias-dependent permittivity and an impedance at least at a temperature equal to an operating temperature of the broadband lambda probe.

5. The broadband lambda probe according to claim 4, wherein the at least one material includes at least one of barium titanate, lead zirconate titanate, and barium strontium titanate.

6. The broadband lambda probe according to one of claim 2, wherein the first sensor electrode is oriented toward the measurement hollow space and the first sensor electrode includes at least one catalytically active material.

7. The broadband lambda probe according to claim 6, wherein the at least one catalytically active material includes at least one of gold, platinum, aluminum, palladium, rhenium, ruthenium, iridium, titanium, titanium nitride, tantalum nitride, and rhodium.

8. The broadband lambda probe according to one of claim 2, wherein the second sensor electrode is directed away from the measurement hollow space and the second sensor electrode includes at least one semiconductor material.

9. The broadband lambda probe according to claim 8, wherein the at least one semiconductor material includes at least one of silicon, germanium, gallium arsenide, indium phosphorus, silicon carbide, and gallium nitride.

10. The broadband lambda probe according to claim 1, wherein the at least one substance is at least one of one hydrogen-containing gas and one nitrogen oxide and the concentration of the at least one substance is present in the capacitive sensor device in the measurement hollow space.

11. The broadband lambda probe according to claim 1, further comprising:

an evaluation device electrically connected to the at least one capacitive sensor device using conductor tracks, the evaluation device configured to determine at least one of a leakage current, a capacitance, a bias-dependent impedance, and a frequency-dependent impedance at the respective capacitive sensor device.

12. A production method for a broadband lambda probe, comprising:

forming an oxygen pump cell in a substrate structure of the broadband lambda probe, the oxygen pump cell configured to transfer oxygen from a measurement hollow space to an external environment of the broadband lambda probe, the substrate structure defining the measurement hollow space, the oxygen pump cell having an outer pump electrode and an inner pump electrode;

forming a Nernst concentration cell in the substrate structure of the broadband lambda probe, the Nernst concentration cell having a Nernst electrode and a reference electrode; and forming at least one capacitive sensor device in the substrate structure, the at least one capacitive sensor device having a capacitance that varies with a change of a concentration of at least one substance in the measurement hollow space.

* * * * *

UNITED STATES PATENT AND TRADEMARK OFFICE
CERTIFICATE OF CORRECTION

PATENT NO. : 9,846,138 B2
APPLICATION NO. : 14/590481
DATED : December 19, 2017
INVENTOR(S) : Martin Schreivogel It is certified that error appears in the above-identified patent and that said Letters Patent is hereby corrected as shown below:

In the Claims

In Column 9, Lines 5-6, Lines 1-2 of Claim 6 should read:
6. The broadband lambda probe according to claim
2, wherein the first sensor electrode is oriented toward the In Column 9, Lines 14-15, Lines 1-2 of Claim 8 should read:
8. The broadband lambda probe according to claim
2, wherein the second sensor electrode is directed away from Signed and Sealed this
Twelfth Day of June, 2018

Andrei Iancu
*Director of the United States Patent and Trademark Office*